(12) United States Patent
Andrews et al.

(10) Patent No.: US 7,252,650 B1
(45) Date of Patent: Aug. 7, 2007

(54) BALLOON CATHETER

(75) Inventors: Geoffrey Thomas Andrews, Cambridge (GB); Robert Adam Snell, Newmarket (GB)

(73) Assignee: Ranier Limited, Cambridge (GB)

( * ) Notice: Subject to any disclaimer, the term of this patent is extended or adjusted under 35 U.S.C. 154(b) by 59 days.

(21) Appl. No.: 09/678,486

(22) Filed: Oct. 4, 2000

Related U.S. Application Data (63) Continuation of application No. 09/241,293, filed on Feb. 1, 1999, now Pat. No. 6,156,254.

(30) Foreign Application Priority Data

Aug. 2, 1996 (GB) ................................. 9616267.2

(51) Int. Cl.
 *A61M 29/00* (2006.01)
(52) U.S. Cl. .............................. 604/103.06; 604/103.09
(58) Field of Classification Search ............. 604/93.01, 604/95.03, 95.05, 96.01, 97.01–97.03, 98.01–99.01, 604/103, 103.03, 103.05–103.09, 103.11–103.13, 604/104, 164.01, 164.03, 264, 523, 524–527, 604/530, 912, 915–916, 918, 920, 921; 606/192, 606/194
See application file for complete search history.

(56) References Cited

U.S. PATENT DOCUMENTS

| | | | | |
|---|---|---|---|---|
| 3,616,199 | A | * 10/1971 | Breslow | ..................... 427/214 |
| 4,115,495 | A | 9/1978 | Hartitz | |
| 4,448,195 | A | * 5/1984 | LeVeen et al. | ............... 604/103 |
| 4,551,293 | A | 11/1985 | Diehl, Jr. et al. | |
| 4,637,396 | A | * 1/1987 | Cook | .......................... 606/194 |
| 4,706,670 | A | * 11/1987 | Andersen et al. | ........... 606/195 |
| 4,921,484 | A | 5/1990 | Hillstead | |
| 4,963,313 | A | 10/1990 | Noddin et al. | |
| 5,087,394 | A | 2/1992 | Keith | |
| 5,171,297 | A | 12/1992 | Barlow et al. | |
| 5,264,260 | A | 11/1993 | Saab | |
| 5,356,591 | A | 10/1994 | Pinchuk et al. | |
| 5,358,487 | A | 10/1994 | Miller | |
| 5,403,340 | A | 4/1995 | Wang et al. | |

(Continued)

FOREIGN PATENT DOCUMENTS

EP 0 102 422 A 3/1984

(Continued)

*Primary Examiner*—Catherine S. Williams
(74) *Attorney, Agent, or Firm*—Wolf, Greenfield & Sacks, P.C.

(57) ABSTRACT

The present invention relates to a balloon portion for a balloon catheter for radially expanding a vessel in the body of a mammal, which catheter comprises a tube portion with a passage therethrough and a hollow expandable balloon portion defined by a fluid impervious wall and secured to the tube portion, which balloon portion can be inflated and deflated by means of a fluid passed through the passage, characterized in that:
  a. the wall of the balloon portion is formed from a flexible substantially fluid impervious material having reinforcing fibers formed integrally with the wall material; and
  b. the balloon portion is preformed to the desired radial diameter at its inflated state having smaller diameter end portions and a wider diameter portion intermediate the said ends and has a substantially uniform wall thickness.

The invention also provides a balloon catheter in which the balloon portion is a balloon of the invention. The invention further provides a method for making the balloon catheter of the invention.

8 Claims, 2 Drawing Sheets

U.S. PATENT DOCUMENTS

| | | | | |
|---|---|---|---|---|
| 5,647,848 A | * | 7/1997 | Jørgensen | 604/103.11 |
| 5,718,861 A | | 2/1998 | Andrews et al. | |
| 5,746,968 A | | 5/1998 | Radisch, Jr. | |
| 5,747,553 A | * | 5/1998 | Guzauskas | 523/115 |
| 5,833,657 A | | 11/1998 | Reinhardt et al. | |
| 5,868,779 A | * | 2/1999 | Ruiz | 606/194 |
| 5,899,935 A | | 5/1999 | Ding | |
| 6,746,425 B1 | * | 6/2004 | Beckham | 604/103.09 |

FOREIGN PATENT DOCUMENTS

| | | |
|---|---|---|
| EP | 186 267 | 7/1986 |
| EP | 0 318 919 A | 6/1989 |
| EP | 0 331 040 A | 9/1989 |
| EP | 0 349 640 A | 1/1990 |
| EP | 0 358 117 A | 3/1990 |
| EP | 425 696 | 5/1991 |
| GB | 2 172 505 | 9/1986 |
| GB | 2 233 562 | 1/1991 |
| IE | 620/89 | 11/1994 |
| WO | 87/00442 | 1/1987 |
| WO | 93/10961 | 6/1993 |
| WO | 95/09667 | 4/1995 |

* cited by examiner

BALLOON CATHETER

This application is a continuation of U.S. application Ser. No. 09/241,293, filed Feb. 1, 1999, now U.S. Pat. No. 6,156,254, the entire contents of which is hereby incorporated by reference in this application, U.S. application Ser. No. 09/241,293 is a continuation of PCT International Application PCT/IB97/00956, filed Aug. 1, 1997, which claims priority to United Kingdom application Ser. No. 9616267.2, filed Aug. 2, 1996.

The present invention relates to a device, notably to a balloon catheter for locally distending a blood or other vessel in a mammal, and to a method of manufacturing a balloon for such a balloon catheter.

BACKGROUND TO THE INVENTION

Balloon catheters are used in surgical techniques, such as angioplasty, in which constrictions in the vascular system (usually coronary arteries) are removed by placing the balloon of the catheter at the site of the constriction and inflating the balloon by applying a gas or fluid to the ballon through the bore of the tubular portion of the catheter to which the balloon portion is attached, typically to a pressure of the order of 5 to 20 bar. This expands the blood vessel radially locally at the balloon to remove the constriction. This technique is well established, but suffers from the disadvantage that 40% of expanded constrictions spontaneously collapse within 24 months of insertion of the balloon. In order to prevent such spontaneous collapse, a rigid tubular reinforcing lining (known as a stent) is commonly placed at the constriction site and expanded radially into position by the balloon catheter so as to provide a more permanent support for the radial expansion of the blood vessel.

Conventional balloon catheters typically comprise a tubular portion carrying the balloon portion at or adjacent the distal end of the tubular portion. The proximal end of the tubular portion is connected to a source of gas or liquid under pressure which is used to expand the balloon portion radially when it has been located at the correct position within a blood vessel. The balloon catheters are of two main types:

those in which the balloon portion is initially of a narrow radial diameter and is expanded radially by the application of pressure to form a larger diameter ballon portion by stretching the wall of the balloon portion and are known as compliant catheters; and those which have a balloon portion, usually made from a thin walled polyethylene terephthalate (PET), which has the required final radial dimension and which is inflated without causing significant radial stretching of the balloon and are known as non-compliant catheters.

In the compliant catheter, that portion of the tube which is to form the balloon portion of the catheter is made from an elastic polymer, so that it can stretch radially to form the larger diameter balloon portion. Usually, such a catheter incorporates reinforcing polymer or metal fibres or braided fibres which not only provide mechanical support to the wall material of the balloon, but also restrict the extent to which the ballon can expand radially. The braiding allows a range of elastic polymers to be used for the wall material and enables high inflation pressures to be used. Typically, such a catheter is formed by laying up the various plies of the structure on a former and removing the former axially to produce a tubular member having a multi-ply wall of substantially uniform thickness. Examples of such compliant catheters are those described in PCT Application No WO 87/00442 and European Patent Application No 0 425 696 A1. However, as described in WO 87/00442, problems arise with such compliant catheters in that the balloon portion moves axially within the blood vessel as the balloon portion is inflated. In order to overcome this, as described in the PCT Application complex design of the relative angles between the fibres in the braiding are required to ensure that as the balloon portion expands other portions of the catheter tube expand axially to retain the balloon portion in the same axial position within the blood vessel. Such forms of catheter are complex and expensive to manufacture and require that the various plies of the structure of the balloon portion are free to move relative to one another to accommodate the changes in geometry of the wall shape as the balloon inflates. Furthermore, as the balloon portion is expanded radially within the blood vessel, the wall thickness reduces, weakening the balloon portion.

With the non-compliant type of catheter balloon, the balloon is made from a substantially non elastic polymer, notably a PET, so that the balloon will expand radially only to its fully deployed state. Such catheters are typically made by blow moulding the desired balloon portion and affixing this to the tube of the catheter. However, during blow moulding the wall thickness of the balloon portion thins as the balloon is expanded to the desired radial dimension. This thinning of the wall results in a fragile balloon portion and also results in excessive thinning, and hence localised extreme weakness, at the points where the fully inflated portion of the balloon merges into the narrow end portions by which the balloon is connected to the tube of the catheter. It is not practical to include re-inforcing braiding into the wall of such a blow moulded balloon, so that the weakness of the wall cannot readily be compensated for. As a result, such a construction cannot be used for balloon catheters where the diameter of the balloon is large compared to the tube to which it is to be attached. Although other methods than blow moulding could be used to form the balloon portion, these are not practical in commercial scale manufacture.

Weaknesses in the wall of the balloon portion result in a risk that the balloon will burst during inflation, notably where high inflation pressures are used. The problems due to the weaknesses in the balloon wall are accentuated when the balloon is used to expand a stent radially since the stent will typically be made from a stainless steel mesh or coil and may have sharp edges which snag the wall of the balloon. As a result, the stent readily punctures the balloon before the stent can be properly placed. It is common to use two or three balloons to place the stent. The use of replacement balloons increases the time of the procedure during which time the arterial blood flow is restricted, thus increasing patient risk and trauma, and incurring a significant additional cost.

We have now devised a form of balloon catheter which reduces the above problems.

SUMMARY OF THE INVENTION

Accordingly, the invention provides a balloon portion for a balloon catheter for radially expanding a vessel in the body of a mammal, which catheter comprises a tube portion with a passage therethrough and a hollow expandable balloon portion defined by a fluid imperious wall and secured to the tube portion, which balloon portion can be inflated and deflated by means of a fluid passed through the passage, characterised in that:

a. the wall of the balloon portion is formed from a flexible substantially fluid impervious material having re-inforcing fibres formed integrally with the wall material; and
b. the balloon portion is preformed to the desired radial diameter at its inflated state having smaller diameter end portions and a wider diameter portion intermediate the said ends and has a substantially uniform wall thickness.

The invention also provides a balloon catheter for radially expanding a vessel in the body of a mammal, which catheter comprises a tube portion with a passage therethrough and a hollow expandable balloon portion defined by a fluid impervious wall and secured to the tube portion, which balloon portion can be inflated and deflated by means of a fluid passed through the passage, characterised in that the balloon portion is a balloon portion of the invention.

By preforming the balloon portion to its inflated diameter, the wall of the balloon does not thin as the balloon is inflated, nor does the axial dimension of the balloon change significantly during inflation, thus reducing the problems of wall thinning and of axial movement of the balloon where the balloon wall stretches during inflation. The re-inforcing fibres are preferably in the form of braiding which limits the extent to which the balloon can be expanded radially and also provides mechanical support to the balloon portion. The balloon portion can thus be made from mechanically weaker, but physiologically more acceptable, polymers than the conventional PET polymers. For example, it is possible to use a softer but more tear resistant polymer, for example a polyurethane, as the major component of the wall of the ballon portion. Since the wall thickness does not reduce significantly during inflation, the problem of balloon puncture by the sharp edge of a stent is further reduced. Alternatives materials to a polyurethane polymer include a styrene butadiene block co-polymer or a butadiene acrylonitrile co-polymer.

The fibre re-inforcement is formed integrally with the material of the wall of the balloon portion so that it moves with the wall as the balloon portion is inflated. Preferably, the fibres are in the form of individual fibres which are wholly encased within the polymer forming the wall. However, the fibres could be at an inner or an outer surface of the flexible wall material, as long as they are in some way bonded or affixed to the wall material so that they are substantially fixed with respect to the wall material and do not slide or move significantly with respect to the wall material. We have found that such a fixed or integral reinforcement provides enhanced support for the wall material and provides improved restraint to radial over-expansion of the wall material as compared to braiding or other reinforcement which is free to move or be rearranged relative to the flexible wall material in response to inflation of the balloon. It will be appreciated that to provide restraint to radial expansion of the balloon, the fibres are made from an inelastic material. However, as described below, the reinforcement may be configured so that limited radial stretching of the balloon may occur so that the reinforcement constructed from the inelastic fibres need not itself be inelastic.

In a preferred embodiment of the invention, the fibres extend around the longitudinal axis of the balloon portion in crossed helical strands to form a braid within the wall material. The braiding could, however have other crossed or woven configurations. For example, the braiding can be provided as a reticulate material with some braids extending longitudinally along the length of the balloon and other braids extending circumferentially around the longitudinal axis of the balloon. However, it is preferred that the braid be configured as opposed overlapping helices of fibres and that the angle between the strands of the fibres and the longitudinal axis of the tube of braided fibres is below the critical angle of the braid when the balloon is in its non-expanded state, that is its rest configuration, and no radial expansion force is applied to the balloon. The critical angle is that angle at which the tube of the braid does not expand or contract radially with the application of radial pressure and is typically about 54 to 55° to the longitudinal axis of the balloon. By forming the braid so that the fibres are inclined at below the critical angle, the balloon can expand radially until the fibres reach the critical angle of inclination. The braid will then resist and further radial expansion of the balloon. The balloon is thus semi-compliant in nature in that some radial stretching of the wall of the balloon can occur, but that is limited to a finite extent by the braiding. Typically, such stretching beyond the fully deployed but not stretched state of the balloon is to from 5 to 15% of the fully deployed diameter of the balloon.

The braiding can be made from any suitable material, notably a stainless steel or polymer fibre, ribbon or wire. Preferably, the material is one which possesses shape memory properties so that the balloon incorporating the material can be caused to change from one configuration to another upon subjecting the balloon to a temperature change. In this way, the change of configuration of the braiding, mesh or fibre re-inforcement can be used to assist the deployment or contraction of the balloon. Thus, for example, a polyester, polyamide or metal braiding or mesh can be formed so that the braiding or mesh adopts a U or S cross-section tube rather than a circular cross-section tube at the rest position of the balloon. Where the memory of the material is activated at high temperature, the braiding or mesh can be formed into the desired configuration and the memory activated prior to incorporation of the braid or mesh into the balloon of the invention. However, it is preferred to use materials whose memory is activated at from 25 to 50° C. so that the balloon and its integral braiding or mesh can be folded longitudinally one or more times to adopt a furled configuration having a U, S or other cross-section. The balloon is caused to retain such a furled shape by subjecting the furled balloon to heat to cause the fibre to memorise the furled shape of the balloon. Typical of materials which possess such a memory function are medical grade stainless steel and polymers such as polyesters, notably PET or polyamides, for example those materials available under the Trade Mark Nitinol from Nitinol Components and Devices Limited of Fremont, Calif., USA. The balloon will thus inherently adopt the furled configuration at the rest condition, which will facilitate insertion of the balloon into the blood vessel and its location at the constriction to be expanded. The balloon can then be expanded to remove the constriction, the braiding or mesh adopting a tubular configuration and limiting the extent of radial expansion of the balloon. When the expansion pressure in the balloon is released, the braiding or mesh will tend to revert to its memorised configuration and will assist furling and removal of the balloon. Whilst the memory configuration has been described above in terms of an S cross-section shape to the furled balloon, other furled shapes may be used if desired. Furthermore, the memorised configuration may be achieved by cooling rather than heating. Other methods for activating the memory of the braid or mesh can readily be devised, for example the heating of the braid or mesh by passing an electrical current through the braid or mesh.

The optimum form and nature of material used to form the re-inforcing fibres of the balloon can readily be determined by simple trial and error tests having regard to the desired geometry of the rest and deployed states of the balloon and the balloon radial expansion forces which the braiding or mesh is to resist. If desired, mixtures of fibres may be used to achieve the desired properties in the overall braid or other re-inforcement in the balloon wall.

For convenience, the invention will be described hereinafter in terms of a braid formed as an opposed double helix of a circular cross-section polyester fibre to provide the re-inforcement of the balloon wall.

As indicated above, the balloon wall is formed from a substantially fluid impervious material. Since the braiding will provide mechanical support and strength to the balloon wall, the wall material can be one which would not on its own survive the expansion conditions. Thus, it is possible to use a softer and physiologically more acceptable polymer than the PET hitherto considered necessary for a non-compliant balloon, for example a vinylic or polyalkylene polymer. A particularly preferred material for use in the construction of the balloon is a polyurethane. If desired the wall of the balloon may be of a composite or laminated construction with an outer layer of a soft polymer, for example a medical grade polyurethane; and an inner layer of a fluid resistant polymer, for example a PET or polyvinylidene chloride. For convenience, the invention will be described hereinafter in terms of a balloon made from a polyurethane.

The balloon of the invention can be of any suitable size and shape having regard to the use to be made of the balloon. However, it will usually be preferred that the balloon adopt a cylindrical configuration when deployed and that it be used upon a tubular portion of the catheter which has an external diameter of from 0.5 to 1.5 mms or more. The external diameter of the deployed but unstretched balloon is typically at least 1.5 times that of the tubular portion of the catheter, for example from 1 to 10 mms. However, since the balloon of the invention does not undergo significant wall thinning or axial movement during expansion to its deployed configuration, it is possible to form balloons of the invention which have an external deployed diameter of 20 to 25 mms or more. Similarly, the balloon can be of any suitable axial length and the invention enables longer balloons to be made than hitherto, for example 300 mms or more. The ability to make such large balloon without the problems of wall thinning or axial movement during deployment expands the range of uses to which such balloon catheters may be put.

The balloon of the invention may embody other features which enhance its efficacy or ease of use. Thus, since the wall of the balloon may be made from a polyurethane polymer in place of the conventional PET, it is possible to incorporate a lubricating adjuvant such a polyvinylpyrrolidone polymer into the polyurethane polymer to impart lubricity to the external surface of the balloon and to prevent the faces of the balloon adhering together. The balloon can thus be more readily fed through the insertion tube and blood vessel to the desired location in the body and can then be readily deployed without the balloon sticking in the furled configuration.

The balloon of the invention can be made by any suitable technique. For example an initial layer of an aqueous dispersion of a polyurethane polymer can be applied to a former and dried to form a layer of polyurethane. The requisite braiding can then be wound upon the layer of polyurethane and an outer layer of polyurethane applied to bond the braiding in position within the polyurethane wall of the ballon. The resultant balloon can then be removed from the former, for example by deflating the former, to provide a balloon having the desired shape and dimensions and having a substantially uniform wall thickness.

However, a particularly preferred method of manufacture comprises forming a tubular balloon having the desired wall thickness and external diameter upon a cylindrical former or mandrel. The resultant tubular balloon is withdrawn axially from the former, which overcomes the problem of forming the former as a deflatable member. The tubular balloon is then stretched axially, for example by clamping the ends of the tube in two clamps which can be moved axially with respect to one another by an hydraulic or pneumatic ram, a screw or camming mechanism or other means. As the tube is stretched axially, its radial diameter is reduced until the internal diameter of the tube is reduced to the external diameter of the tubular portion of the catheter upon which the balloon is to be mounted. The terminal portions of the tube are then subjected to the necessary conditions, for example heat, to cause the reduced diameter of the stretched tube to become fixed. For example, the memory of the braiding can be activated so that the ends of the tube adopt the configuration at this smaller diameter to the tube. For example, the terminal portions of the stretched tube can be exposed to a flame or hot air blast or heated blocks can be applied to the end of the tube to cause the braid memory to be activated and to sever the tube from the clamping/stretching mechanism. Alternatively, the ends of the stretched tube can be heated to relax stresses within the structure of the wall of the tube and/or to cause some or all of the polymer within the wall to flow to adopt the narrower diameter. The ends of the tube can be cooled to fix the ends of the tube in the narrower diameter form. In yet another process, a solvent may be applied to the ends of the tube in order to allow the polymer to flow and relieve the internal stresses produced by stretching the tube, after which the solvent may be dried from the ends of the tube to stop further flow of the polymer.

The tube will thus adopt a configuration having terminal portions or cuffs with the desired small diameter and an intermediate portion having the desired larger diameter for the balloon. Such a method provides a simple and effective method for forming a balloon having substantially uniform wall thickness.

Accordingly, for another aspect, the present invention provides a method for making a balloon of the invention which method comprises;

a. forming a generally tubular member having the wall composition of the balloon portion of the catheter of the invention and having the external diameter of the balloon portion in its radially deployed state:

b) stretching the tubular member axially until the inner diameter of the tubular member adjacent the ends thereof is reduced to or proximate to the external diameter of the catheter tube upon which it is desired to mount the balloon; and c) applying a process to at least one of the end portions of the axially stretched tube in order to set the reduced inner diameter of that end portions of the stretched tubular member; and d) relieving the axial stretch of the tubular member in order to allow the portion of the tubular member intermediate the reduced dimension end portions to expand radially to provide the wider diameter portion of the balloon of the invention.

The axial stretching of the tubular member can take place with a cylindrical former having the diameter to which it is desired to reduce the end portions of the member inserted into the tubular member; and the axial stretching is carried out until the tubular member is a snug fit upon the former.

The invention has been described above in terms of a balloon portion having both ends open for mounting on the tubular portion of the catheter. However, it is within the scope of the present invention to form one end of the balloon as a closed end for mounting terminally upon the distal end of the catheter tube. Such a closed end can readily be formed by any suitable technique. Thus, a tapered nose piece can be inserted into the open distal end of the balloon; the balloon can be formed with a closed end during manufacture; or the closed end can be formed by heat sealing the distal end of the balloon, for example as part of the severing of the balloon from the clamping/stretching mechanism described above.

If desired the balloon can be subjected to further treatment after being formed into its basic cylindrical form. Thus, the balloon can be configured into its furled configuration, for example by forming longitudinally extending folds in the wall material to give the S cross-section to the balloon described above, and exposing the balloon to conditions, for example heating, to cause the memory of the braid within the wall of the balloon to adopt the furled configuration.

The balloon catheter of the invention can be used in the same manner as a conventional balloon catheter. However, since the balloon can be deployed from its rest to its expanded configuration with little or no reduction in its wall thickness, the balloon can be inflated using a gas or liquid at higher pressures than would normally be acceptable with a conventional balloon, for example 10 to 20 bar. The ability to use such higher pressures enables the user to achieve full inflation of the balloon against the restraint of the braiding more consistently then where lower pressures are used, thus ensuring that the desired dilation of the constriction of the blood vessel is achieved. The ability of the balloon to resist snagging and tearing by a metal stent enables such a stent to be positioned and expanded with fewer balloon replacements than hitherto. The ability to use high pressures also enables the stent to be expanded to a specified diameter more consistently than hitherto.

DESCRIPTION OF THE DRAWINGS

The invention will now be further described by way of example with reference to the accompanying drawings, in which.

DESCRIPTION OF THE PREFERRED EMBODIMENT

FIGS. 1 to 5 illustrate how a first embodiment of a balloon for the balloon catheter of the present invention is formed. A hollow tube 1 is formed of a flexible and resilient elastomeric material 2, in this example a polyurethane. The material 2 is reinforced with braided PET mono-filaments 3, half of which trace out right-handed parallel helixes, and the other half of which trace out left handed parallel helixes. The helixes are crossed at points, but the PET fibres are not bonded to each other at these points. The PET filaments 3 are completely surrounded by the polyurethane. The tube of this example has an outer diameter of 6 mm, an inner diameter of 5.9 mm, and a length of 25 mm. These dimensions may be larger or smaller, depending on the application for the balloon catheter. The PET fibre thickness in this example is about 40 μm, which can readily be completely contained within the wall thickness of about 100 μm for the balloon even where the fibres cross over one another. Smaller or larger balloons will have correspondingly smaller or larger diameter fibres, for example from 25 μm to 80 μm, with the wall thickness being approximately double the thickness of the fibre.

Figure 1:
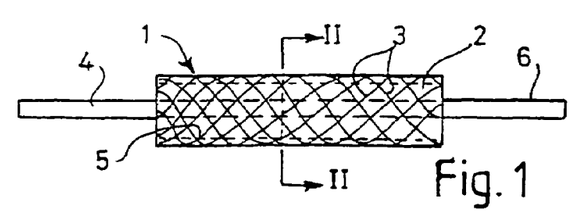
FIG. 1 is a side view of a PET mono-filament reinforced polyurethane tube, through which a rod former has been inserted.
Figure 2:
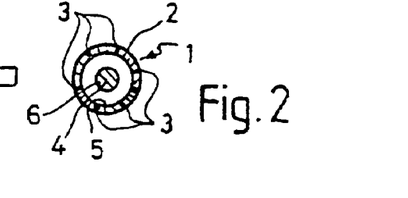
FIG. 2 is a cross-section through line II—II of FIG. 1.
Figure 3:
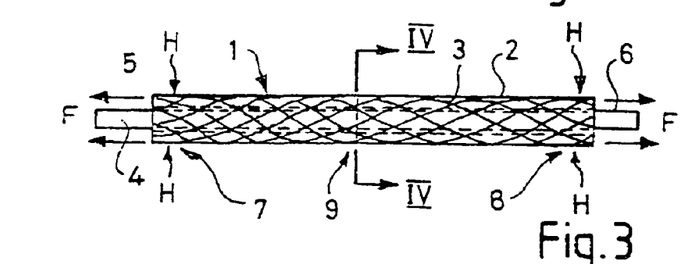
FIG. 3 is a side view the tube and former of FIG. 1, with the tube stretched lengthwise along the former, and with heat applied to the ends of the tube.
Figure 4:
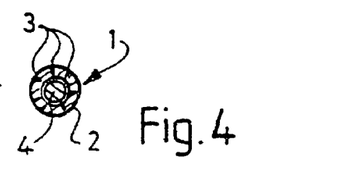
FIG. 4 is a cross-section through line IV—IV of FIG. 3.

A stainless steel cylindrical rod former 4 with an outer diameter of 1.8 mm has been passed through the centre axis of the cylindrical tube 1. FIG. 3 shows how, when a stretching force, indicated schematically by the straight arrows F, is applied to the ends of the tube 1, the tube will stretch, lengthen and narrow until an inner surface 5 of the tube is in contact with an outer surface 6 of the rod 4.

Heat may then be applied to ends 7, 8 of the tube 1, the ends being separated by a middle portion 9, for example with a hot air gun (not illustrated), as indicated by schematically by the wavy arrows H. It has been found experimentally that a hot air gun with an air temperature of about 350° C. directed at the end portions 7, 8 for about 5 seconds will cause the polyurethane material 2 to undergo a limited plastic deformation or flow that allows polymer chains to re-orient and so relieve the tension at the end portions caused by the stretching. The PET braid 3 is also heated above its glass transition temperature, and so some reorientation of the polymer in the braid also takes place, helping to the set the stretch of the end regions.

Once the heat source is removed, the end portions 7, 8 quickly cool down aided by thermal conduction from the stainless steel rod 4. After cooling the rod may be removed from inside the tube.

Figure 5:
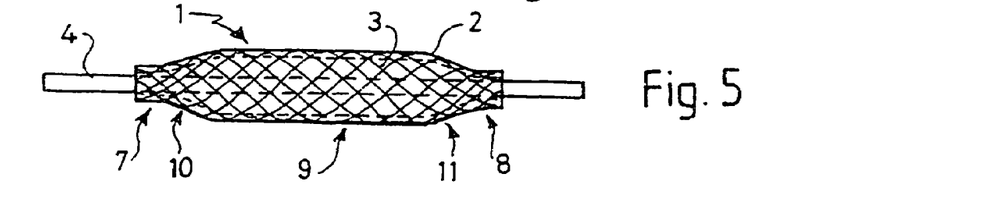
FIG. 5 is a side view of the tube of FIG. 3, after the stretching has been released to form a bulbous middle portion with narrower end portions.
Figure 6:
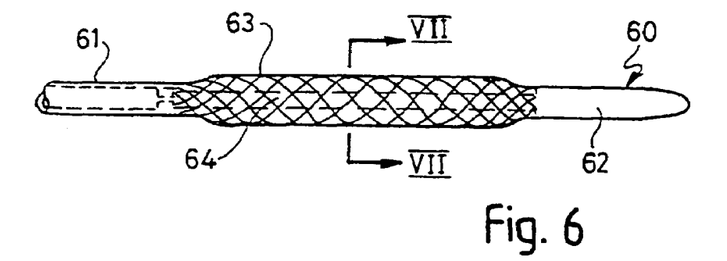
FIG. 6 is a side view of a first embodiment of a balloon catheter with a balloon formed from the tube of FIGS. 1 to 5 attached to a catheter probe.

When the stretching force F is removed, the centre section, which has not been heated sufficiently to cause the polyurethane material 2 to flow, will spring back to the same diameter the tube had prior to stretching and heating. The end portions 7, 8, however, remain at the reduced dimensions resulting from the stretching. There are smooth transition portions 10, 11 between the ends 7,8 and the middle 9 portions, at which the outer and inner diameters of the tube taper smoothly between minimum and maximum dimensions and the wall thickness of the bulbous portion and the transition portions is substantially uniform without localised thinning. The total length of the formed tube may be selected to be between about 30 mm to about 35 mm.

Once the tube 1 is formed, it may be incorporated with an otherwise conventional catheter 60, as shown in FIGS. 6 to 10. The catheter has a hollow flexible stem 61 with a passage for the passage of air, and a solid end 62 which may be inserted into a body vessel such as an artery. The end could, however, be a closed end of the balloon. Between the stem 61 and the end 62, the tube is bonded to form the balloon portion 63 of the catheter. An axial support 64 may be mounted axially within the balloon 63 to retain the balloon axially deployed.

Figure 7:
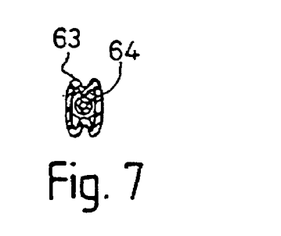
FIG. 7 a cross-section of the balloon catheter, through line VII—VII of FIG. 6.
Figure 8:
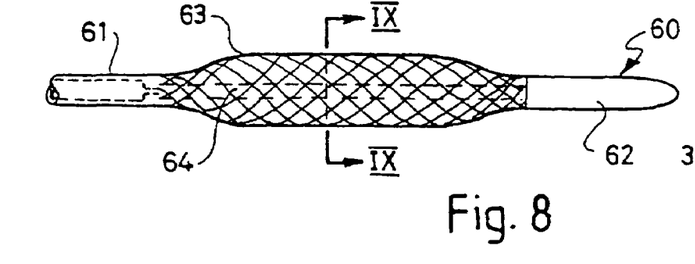
FIG. 8 is a side view of the balloon catheter of FIG. 6, after inflation of the balloon.
Figure 9:
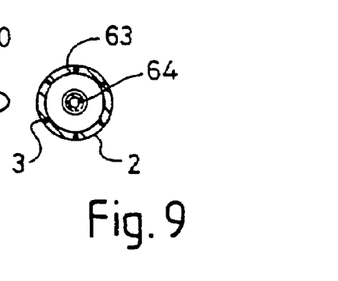
FIG. 9 is a cross-section of the balloon catheter, through line IX—IX of FIG. 8.

As shown in FIG. 7, the balloon portion 63 can be folded longitudinally so as to furl the balloon for insertion into a blood vessel in a mammal. Where the braiding in the balloon wall has a memory property, the furled balloon may be heated to set the material of the braid in the furled configuration of the balloon. The balloon 63 remains deflated until air is pumped through the stem 61 into the balloon, as shown in FIGS. 8 and 9. The flexible polyurethane envelope of the balloon is readily expanded with air under about 5 to 10 bar pressure until the PET reinforcement 3 becomes taut, whereupon the balloon will not expand further.

Figure 10:
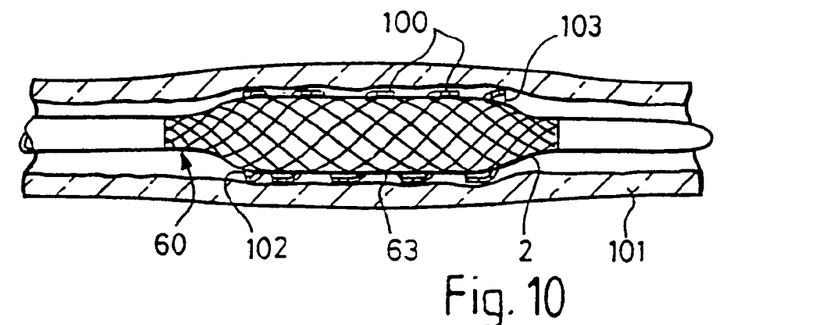
FIG. 10 is a side view of the balloon catheter of FIG. 6 placing a stent at a constricted point of a blood vessel in the body of a mammal.

FIG. 10 shows the balloon catheter 60 being used to expand and place a stent 100, which is a coil of stainless steel at a point in a body vessel 101 which had been constricted. The coil has ends 102,103 with relatively sharp edges. The polyurethane 2 material of the balloon 63 is not readily pierced or torn by contact with the coil 100.

Figure 11:
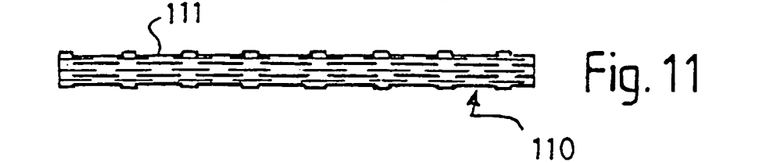
FIGS. 11 to 16 illustrate and alternative form of the balloon of the invention in which a shape memory metal mesh is used in place of the PET braid to provide the re-inforcement to the polyurethane wall of the balloon.
Figure 12:
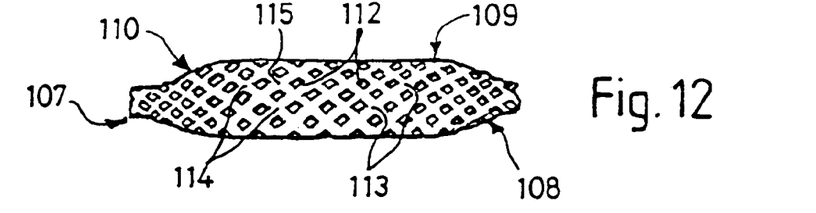

In place of the PET fibre braiding used in the device just described, the balloon portion of the catheter may contain a shapes memory metal mesh 110. This can be formed from a cylindrical tube shown in FIG. 11 which has had a number of longitudinal thin parallel slots 111 laser-cut through the wall of the cylinder. Such meshes may be obtained from Nitinol Components and Devices, Ltd. of Fremont, Calif., USA. In this example, there are twelve aligned rows of slots 111, alternate rows being offset out of phase with each other.

The wall thickness of the shape memory metal may be selected to be between about 25 μm to about 75 μm. This is thick enough to give sufficient mechanical performance to serve as reinforcement in a balloon, and also thin enough to allow the shape memory metal mesh to be encapsulated in a balloon, as will be described below.

Shape memory metals such as nitinol are pliable, and so the mesh 110 may be deformed in the following manner. The length and spaces of the slots is such that the shape memory metal mesh can be expanded laterally to form a mesh with a shape is similar to that the PET braid used in the devices of FIGS. 1 to 10; that is, with a total length of about 35 mm and with a bulbous middle portion 119 about 6 mm in diameter between narrower end portions 117,118. Slot edges 112 define approximately helical braids 113,114 which cross each other at nearly right angles. In this sense the shape memory metal mesh also has a similar braid to the PET braid, except that the shape memory metal helixes are, of course, joined at crossing points 115.

Figure 13:
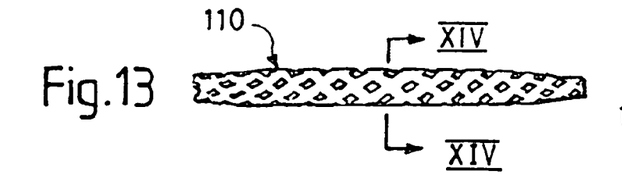
Figure 14:
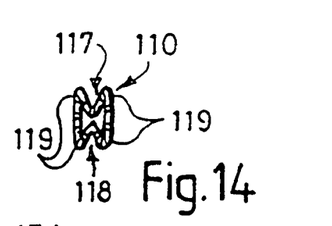

FIGS. 13 and 14 show how the shape memory metal mesh 110 may then be folded to form a similar compact shape to that achieved by the deflated polyurethane balloon of FIG. 7. Two longitudinal fold lines 117,118 along opposite sides of the expanded mesh bulbous middle portion 109 define what is referred to herein as a "star" shape with four lobes 119 of mesh which reduce the cross-sectional dimensions of the mesh.

The shape memory metal may then be treated at an elevated temperature of between 300° C. and 500° C., depending on the composition of the metal alloy, in order to fix the memory of the shape in the metal.

The shape memory metal mesh 110 may then be cooled to room temperature, and a tough polyurethane coating applied. Although not illustrated, this may be done by moulding the mesh around a form, for example a wax form, with a shape corresponding to that of the bulbous shape of FIG. 12, and then dip coating the mesh in an uncured polyurethane resin prior to curing the polyurethane. The wax form may then be melted away.

Figure 15:
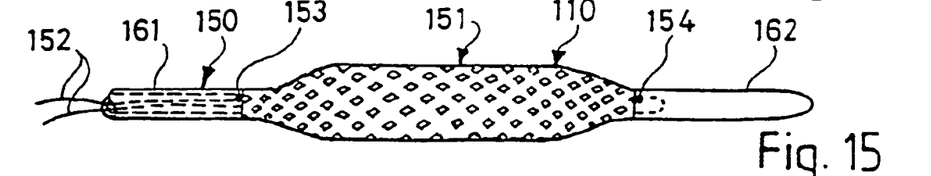
Figure 16:
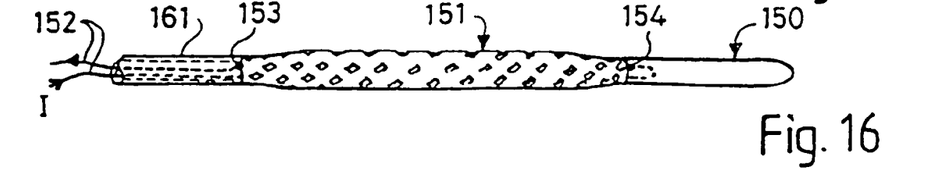

Once the shape memory metal mesh has been coated, it may be assembled as a balloon 151 with a catheter 150, as illustrated in FIGS. 15 and 16. The catheter 150 is similar to that described above, except that a pair of wires 152 pass through a hollow stem 161 and are electrically connected at a pair of points 153,154 at opposite ends of the shape memory metal mesh 110.

FIG. 15 shows the balloon 151 expanded with air, as it would be when placing a stent in a body vessel (not illustrated). Whilst the shape memory metal is pliable, it is rigid enough to resist longitudinal deformation along the stands of the helixes 113,114, and so resists over-inflation.

When air is pumped out of the balloon, the balloon will tend to collapse. At the same time, an electric current I is passed through the wires 152 sufficient to heat up the shape memory metal to above its transition temperature, which in this example, is chosen to be about 45° C. The shape memory metal then recalls its fixed shape of FIGS. 13 and 14, and collapses neatly, so folding the balloon as illustrated in FIG. 16. The balloon catheter may then be readily withdrawn from a body vessel.

The invention claimed is:

1. A hollow radially expandable balloon member comprising an intermediate portion located between terminal portions which have a diameter smaller than the intermediate portion and having a fluid impervious wall, which balloon member is for use with a catheter for radially expanding a vessel in the body of a mammal, which catheter comprises a tube portion with a passage therethrough and which is adapted to have the hollow expandable balloon member secured to the tube portion by the smaller diameter terminal portions, whereby the balloon member can be inflated and deflated by a fluid passed through the passage of the catheter wherein:
   a. the wall of the balloon member has a substantially uniform thickness and is formed from a flexible substantially fluid impervious material having reinforcing fibres in a braided arrangement provided integrally with the wall material, which fibres act to limit the maximum radial expansion of the balloon member; and
   b. the intermediate portion of the balloon member has a radial diameter, in a deflated state, which corresponds substantially to a radial diameter of the intermediate portion of the balloon member at a maximum radially expanded state, whereby the balloon member can be inflated to its maximum radial expansion state as limited by the fibres within the wall material without causing substantial stretching of the wall material, such that the balloon member is non-compliant.

2. A balloon member as claimed in claim 1, wherein the reinforcing fibres are provided by a polymer or metal mesh.

3. A balloon member as claimed in claim 1, wherein the reinforcing fibres are made from or contain a material having shape memory properties.

4. A balloon member as claimed in claim 1, wherein the reinforcing fibres are filaments of a polyester polymer.

5. A balloon member as claimed in claim 1, wherein the braided fibres are in the form of two opposed helices of filaments.

6. A balloon member as claimed in claim 5, wherein the braid has a critical angle and the opposed helices are oriented to one another at or adjacent to said critical angle of the braid.

7. A balloon member as claimed in claim 1, wherein the flexible wall material is a polyurethane.

8. A balloon catheter for radially expanding a vessel in the body of a mammal, which catheter comprises a tube portion with a passage therethrough and a hollow expandable balloon portion defined by a fluid impervious wall and secured to the tube portion, which balloon portion can be inflated and deflated by a fluid passed through the passage, wherein the hollow expandable balloon portion is a hollow expandable balloon member comprising an intermediate portion located between terminal portions which have a diameter smaller than the intermediate portion and having a fluid impervious wall, which catheter is adapted to have the hollow expandable balloon member secured to the tube portion by the smaller diameter terminal portions, whereby the balloon member can be inflated and deflated by a fluid passed through the passage of the catheter, wherein:

a. the wall of the balloon member has a substantially uniform thickness and is formed from a flexible substantially impervious material having reinforcing fibres in a braided arrangement provided integrally with the wall material, which fibres act to limit the maximum radial expansion of the balloon member; and b. the intermediate portion of the balloon member has a radial diameter, in a deflated state, which corresponds substantially to a radial diameter of the intermediate portion of the balloon member at a maximum radially expanded state, whereby the balloon member can be inflated to its maximum radial expansion state as limited by the fibres within the wall material without causing substantial stretching of the wall material, such that the balloon member is non-compliant.

* * * * *

UNITED STATES PATENT AND TRADEMARK OFFICE
CERTIFICATE OF CORRECTION

PATENT NO. : 7,252,650 B1
APPLICATION NO. : 09/678486
DATED : August 7, 2007
INVENTOR(S) : Geoffrey T. Andrews et al.

It is certified that error appears in the above-identified patent and that said Letters Patent is hereby corrected as shown below:

On the cover page of the issued patent:

Please insert at the end of section (63):

--U.S. application no. 09/241,293 is a continuation of PCT/IB97/00956, filed on August 1, 1997.--

Signed and Sealed this

Twentieth Day of November, 2007

JON W. DUDAS
*Director of the United States Patent and Trademark Office*